US011690771B2

(12) United States Patent
Ernstoff (10) Patent No.: US 11,690,771 B2
(45) Date of Patent: Jul. 4, 2023

(54) HYGIENIC BARRIER

(71) Applicant: Novel Academic Technological Environments LLC, Chester, CT (US)

(72) Inventor: Marty L. Ernstoff, Chester, CT (US)

(73) Assignee: Novel Academic Technological Environments LLC, Chester, CT (US)

( * ) Notice: Subject to any disclaimer, the term of this patent is extended or adjusted under 35 U.S.C. 154(b) by 0 days.

(21) Appl. No.: 17/171,496

(22) Filed: Feb. 9, 2021

(65) Prior Publication Data

US 2021/0401651 A1    Dec. 30, 2021

Related U.S. Application Data

(60) Provisional application No. 63/048,050, filed on Jul. 3, 2020, provisional application No. 63/044,907, filed on Jun. 26, 2020.

(51) Int. Cl.
*A61G 10/00* (2006.01)
*A61B 46/23* (2016.01)

(52) U.S. Cl.
CPC ............ *A61G 10/005* (2013.01); *A61B 46/23* (2016.02)

(58) Field of Classification Search
CPC ...... A61G 10/00–04; A61G 11/00–009; A61B 46/00; A61B 46/20; A61B 46/23; A61B 2046/205; A61B 90/40; A47C 29/003; A47C 29/006; A47K 3/38; Y10S 128/917
See application file for complete search history.

(56) References Cited

U.S. PATENT DOCUMENTS

| 27,007 | A | * | 1/1860 | Palmer | A47C 29/006 |
| | | | | | 135/90 |
| 90,054 | A | * | 5/1869 | Searle | A47C 29/006 |
| | | | | | 135/90 |
| 851,429 | A | * | 4/1907 | Noble | A47C 29/006 |
| | | | | | 135/90 |
| 2,497,832 | A | * | 2/1950 | Fairlamb | A61G 10/04 |
| | | | | | 135/156 |
| 3,800,790 | A | | 4/1974 | Collins | |
| 3,889,667 | A | | 6/1975 | Collins | |
| 4,081,306 | A | | 3/1978 | Depriest et al. | |
| 4,323,062 | A | | 4/1982 | Canty | |

(Continued)

FOREIGN PATENT DOCUMENTS

| AU | 695770 | 12/1998 |
| CA | 2847495 | 3/2013 |

(Continued)

OTHER PUBLICATIONS

Machine translation of WO 2009109055, obtained from Espacenet on Apr. 30, 2021 (Year: 2009).*

*Primary Examiner* — Thaddeus B Cox
(74) *Attorney, Agent, or Firm* — Levine Bagade Han LLP (57) ABSTRACT

Personal protective equipment including hygienic barriers and methods of use to provide an improved barrier between a patient and a caregiver; where such barriers include a reinforced region and an enclosure portion, where the enclosure portion extends beyond the reinforced region such that when suspended above the patient, in a deployed configuration, the enclosure portion hangs down from the reinforced region through a force of gravity to form an enclosure space.

21 Claims, 10 Drawing Sheets

(56) References Cited

U.S. PATENT DOCUMENTS

| | | |
|---|---|---|
| 4,335,712 A | 6/1982 | Trexler |
| 4,367,728 A | 1/1983 | Mutke |
| 4,905,710 A | 3/1990 | Jones |
| 4,953,566 A | 9/1990 | Garren |
| 5,038,798 A | 8/1991 | Dowdy et al. |
| 5,042,507 A | 8/1991 | Dowdy |
| 5,170,804 A | 12/1992 | Glassman |
| 5,316,541 A | 5/1994 | Fischer |
| 5,341,821 A | 8/1994 | Dehart |
| 5,342,121 A * | 8/1994 | Koria ............... A61G 10/005 312/1 |
| 5,409,018 A | 4/1995 | Mills |
| 5,471,999 A | 12/1995 | Mills |
| 6,126,631 A | 10/2000 | Loggie |
| 6,179,819 B1 | 1/2001 | Haswell |
| 7,037,254 B2 | 5/2006 | O'connor et al. |
| 7,044,132 B2 | 5/2006 | Masini |
| 7,316,233 B2 | 1/2008 | Auerbach et al. |
| 7,343,919 B2 | 3/2008 | Czajka et al. |
| 7,958,894 B2 | 6/2011 | Katoh et al. |
| 8,245,713 B2 | 8/2012 | Paschal et al. |
| 8,286,637 B2 | 10/2012 | Kaska |
| 8,371,306 B2 | 2/2013 | Haines et al. |
| 9,814,526 B2 | 11/2017 | Sloth et al. |
| 9,993,310 B2 | 6/2018 | Pecora |
| 10,251,801 B2 | 4/2019 | Breegi et al. |
| 10,265,133 B1 | 4/2019 | Mcclellan |
| 10,729,507 B2 | 8/2020 | Beale et al. |
| 2003/0085147 A1 | 5/2003 | Gabriele |
| 2008/0283064 A1 | 11/2008 | Block et al. |
| 2011/0301459 A1 | 12/2011 | Gharib |
| 2016/0166323 A1 | 6/2016 | Tylka |
| 2020/0237470 A1 | 7/2020 | Aljuri et al. |
| 2021/0315757 A1 * | 10/2021 | Nguyen ............... A61G 7/05 |

FOREIGN PATENT DOCUMENTS

| | | | |
|---|---|---|---|
| CN | 111173355 A * | 5/2020 | ............ A61G 10/00 |
| EP | 3484404 | 5/2019 | |
| EP | 3513762 | 7/2019 | |
| EP | 3661447 | 6/2020 | |
| GB | 2434546 A * | 8/2007 | ............ A61B 90/40 |
| JP | 5618169 B2 * | 11/2014 | |
| WO | WO-2006110797 A2 * | 10/2006 | ............ A61G 11/009 |
| WO | WO 2009/109055 | 9/2009 | |
| WO | WO-2009109055 A1 * | 9/2009 | ............ A61B 90/40 |
| WO | WO 2016/010849 | 1/2016 | |
| WO | WO 2018/014003 | 1/2018 | |
| WO | WO-2018144809 A1 * | 8/2018 | ............ A61G 11/00 |
| WO | WO 2019/025924 | 2/2019 | |
| WO | WO-2021216611 A1 * | 10/2021 | ............ A61B 90/40 |

* cited by examiner

HYGIENIC BARRIER

CROSS-REFERENCE TO RELATED APPLICATIONS

This application is a non-provisional of provisional application Nos. 63/044,907 filed Jun. 26, 2020, and 63/048,050 filed Jul. 3, 2020, the entirety of each of which is incorporated by reference.

BACKGROUND OF THE INVENTION

The use of personal protective equipment (PPE) such as facemasks, surgical gowns. surgical drapes, bouffant caps, etc. is fundamental practice in the healthcare industry intended to not only help prevent the spread of disease but also intended to protect both healthcare provider and patients from exposure to potential pathogens, microorganisms, or other infectious substances. Such PPE protects by filtering or creating a barrier to airborne contaminants and microorganisms.

The need for PPE especially increases in those situations where a patient is suspected of carrying a contagious disease and is being examined by a healthcare worker. The need exists during ordinary flu seasons. However, the need for PPE exponentially increases during pandemics, where it is imperative to protect the health of healthcare workers to ensure the integrity of the healthcare system.

However, current PPE's suffer drawbacks in that they do not isolate contamination from a patient being examined or treated. PPE is often pressed against tissue on the face or head and can produce discomfort for those workers who must continually maintain the PPE in a tight fit. In addition, PPE can be time consuming to don, and in many cases may not provide sufficient protection. PPE's are often uncomfortable, particularly for those healthcare providers who may require layers of PPE's over their face and wear them for prolonged periods. These PPE's can inhibit vision and serve as a distraction to providers. Many medical procedures and examinations involve the risk of fluid from the patient being dispersed in an area surrounding the patient. While traditional PPE provides some protection for the healthcare worker, this protection can be cleaned and disinfected between patients as a matter of procedure. This creates a risk of improper cleaning of some surfaces, and attendant transmission risks for the health care worker or any other individual that subsequently enters the area.

In one example, examination of patients during endoscopic procedures commonly allows leakage of body fluid onto the surrounding surfaces as well as aerosolization of these fluids into the immediate airspace, further exposing providers to contamination. Additionally, many procedures require the removal of the mask or other PPE from the patient, thereby eliminating another protective barrier for the provider. Additionally, endoscopic procedures have been found to aerosolize these fluids which contain microbes and increase infectivity to those exposed. These particles can linger in the air for hours after the procedure. Moreover, examination procedures where a caregiver must inspect a mouth or other body cavity of a patient do not allow for the patient to wear effective PPE to eliminate such spread of respiratory/digestive fluids or other fluids or bodily substances.

Spreading diseases by pathogenic microorganisms, such as bacteria, viruses, parasites or fungi; indirectly, from one person to another via surfaces has always been a risk. But the recent pandemic highlighted the risk of an individual that can be a carrier of a pathogenic microorganisms while asymptomatic. That is, while the person is a carrier of pathogenic microorganisms, the individual does not yet display signs or symptoms of any disease. While current PPE is designed to protect the individuals wearing the PPE, it is not currently suited for patients being examined by medical caregivers. Moreover, current PPE, in general practice (i.e., outside of the context of clean rooms and changes of hazmat suits between patients) is inadequate to fully protect or isolate the risk.

Accordingly, in view of the risk of exposure to pathogenic microorganisms, there remains a need for PPE's that minimize the spread of fluid and other particles without increasing patient discomfort and/or reduce the effectiveness of a caregiver to examine efficiently and to interact with a patient.

Figure 1:
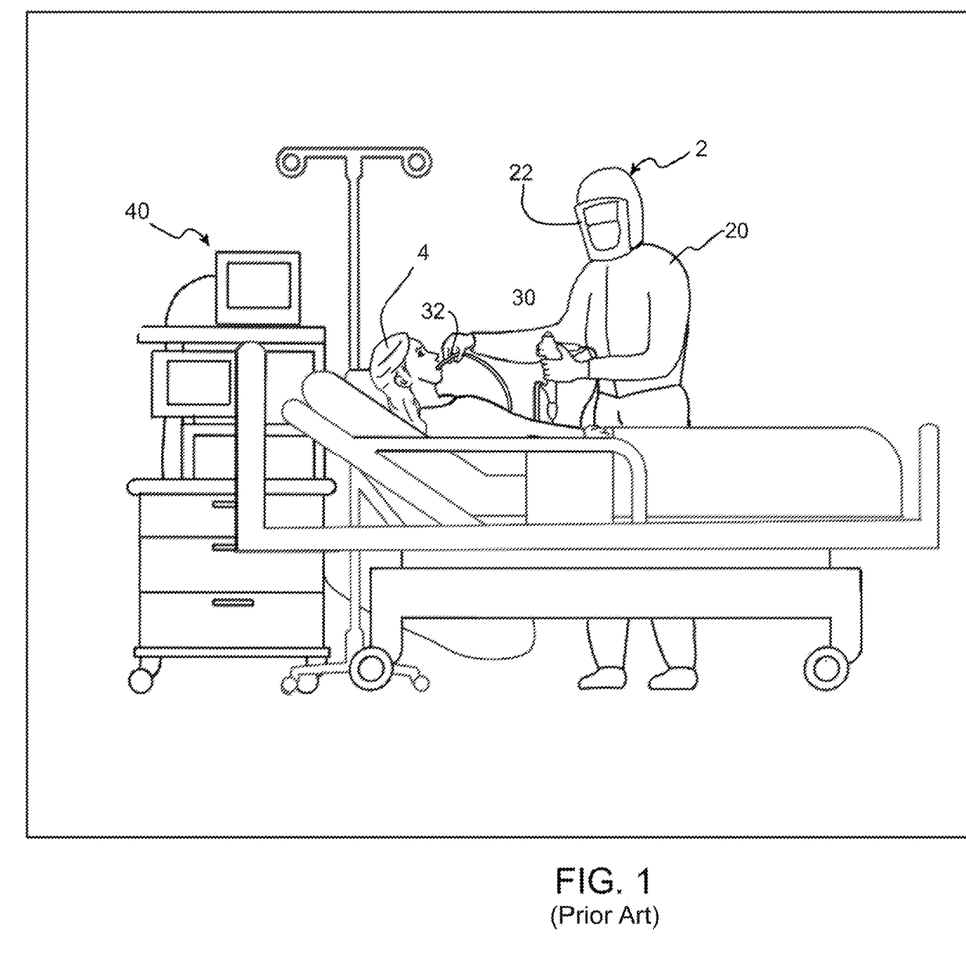
FIG. 1 illustrates one example of a conventional approach where a caregiver attends to a patient.

FIG. 1 illustrates one example of a conventional approach where a caregiver 2 attends to a patient 4. The illustration shows the caregiver 2 wearing PPE 20 and a mask 22 and inserting an endoscope 32 into the patient while manipulating a handle 30 of the endoscope 32. While the patient 4 is shown in a bed, the patient can be seated or standing during an examination. As discussed above, the PPE 20 and mask 22 protects the caregiver 2 from respiratory fluids produced by the patient 2 and or fluids generated during the procedure. However, any respiratory or bodily fluids are still able to disperse to unprotected surfaces, such as equipment 40, within the examination room.

BRIEF SUMMARY OF THE INVENTION

The illustrations and variations described herein are meant to provide examples of the methods and devices of the invention. It is contemplated that combinations of aspects of specific embodiments or combinations of the specific embodiments themselves are within the scope of this disclosure.

The present disclosure includes hygienic barriers for suspending over a patient to limit a spread of fluids or bodily substances from the patient, including but not limited to respiratory fluids, digestive elements, blood, fecal matter, etc.

In one variation, a hygienic barrier includes a reinforced region and an enclosure portion, where the enclosure portion extends beyond the reinforced region such that when suspended above the patient, in a deployed configuration, the enclosure portion hangs down from the reinforced region through a force of gravity to form an enclosure space, where at least the enclosure portion allows for direct visualization of the patient therethrough; the enclosure portion having a patient-side on an interior of the enclosure space and a caregiver-side exterior to the enclosure space; at least one arm opening located in the enclosure portion, the at least one arm opening includes an arm sleeve, the arm sleeve having a near end, a far end, and a sleeve wall extending therebetween, the near end being joined to the enclosure portion about a respective arm opening, where the sleeve wall extends within the enclosure space such that the far end can be movably positioned in the enclosure space when a caregiver extends a hand into at least one arm opening from the caregiver-side, where the sleeve and the enclosure portion maintain a fluid barrier between the patient and the caregiver; and at least one tool opening in the enclosure portion that allows an instrument to be passed from the caregiver-side through the enclosure portion to the patient-side and into the enclosure space.

The materials forming the barrier (especially the patient side of the enclosure portion) can be treated to have any desired effect. For example, the material can include a hydrophilic coating, a hydrophobic coating, antimicrobial, or any splash resistance feature.

In an additional variation, a hygienic barrier can comprise a reinforced region and enclosure portion formed from one or more continuous sheets of material, and wherein the reinforced region includes a reinforcement support structure.

In another variation of a hygienic barrier, the reinforced region includes a material having a pre-determined shape, wherein the enclosure portion is sealingly joined or otherwise attached to the reinforced region. For example, such a reinforced region can have a shape selected from a group consisting of a planar shape, a concave shape, and a polygonal shape.

Variations of the hygienic barriers disclosed herein can include at least one tool opening is located adjacent to the at least one arm opening.

In certain variations of hygienic barriers disclosed herein, the reinforced region comprises a frame structure adjacent to the reinforced region.

In additional variations, the hygienic barrier can include a reinforced region that bends to a lesser degree than the enclosure portion to create an increased area of the enclosure space adjacent to the reinforced region.

Variations of the barrier can include arms sleeves having a far end that comprises a glove shape with at least two opposable portions. For example, some glove shape can comprise four finger portions and a thumb portion, a mitten shape or a simple closed sleeve.

In some variations of hygienic barriers, one or more tool openings can further include a valve structure located in the tool opening. In additional variations, the tool opening can include a temporary barrier such as a perforated cover, a flap, or two or more overlapping layers of material.

In another variation, a hygienic barrier can include an arm sleeve having a far end that comprises a hand opening surrounded by an elastic portion, such that when the caregiver extends the hand into the arm opening and through the hand opening, the elastic portion causes the sleeve wall to close about the hand or an arm of the caregiver.

Additional variations of hygienic barriers can include an outer perimeter of the enclosure portion that is weighted relative to an inner perimeter of the enclosure portion.

The barriers described herein can include at least one or more pockets on the caregiver-side of the enclosure portion, on the patient-side of the barrier, or on both sides.

It is noted that the hygienic barriers described herein include enclosure portions that are frameless to permit observation of the patient as well as navigation of the arm sleeves to attend to the patient.

The hygienic barriers described herein can also include one or more attachment arms coupled to the reinforced region, where the attachment arm can be detachably coupled to an external structure to suspend the hygienic barrier.

The present disclosure also includes methods for establishing a hygienic barrier between a caregiver and a patient. For example, such a method can include suspending a reinforced section of a sheet of material above the patient such that gravity causes an enclosure portion of the sheet of material to hang down from the reinforced section to form an enclosure space about the patient, where a patient-side of the sheet of material is located on an interior of the enclosure space and a caregiver-side of the sheet of material is exterior to the enclosure space; wherein the enclosure portion includes one or more arm openings, and at least one of the one or more arm openings includes an arm sleeve having a near end, a far end, and a sleeve wall extending therebetween, the near end being joined to the sheet of material about a respective arm opening, where the sleeve wall extends within the enclosure space; wherein the enclosure portion includes at least one tool opening that allows an instrument to be passed from the caregiver-side through the sheet of material to the patient-side and into the enclosure space; and wherein the caregiver can insert a hand into the sleeve wall through the arm opening and to the far end allowing for the caregiver to manipulate the instrument while the sleeve wall and the sheet of material maintains the hygienic barrier between the caregiver and the patient allowing the caregiver to attend to and directly visualize the patient through the hygienic barrier.

Another variation of a method under the present disclosure includes methods for a caregiver to interact with a patient through a hygienic barrier. For example, such a method can include suspending a reinforced section of a sheet of material such that gravity causes an enclosure portion of the sheet of material to hang down from the reinforced section to form an enclosure space, such that a patient-side of the sheet of material is located on an interior of the enclosure space and a caregiver side of the sheet of material is exterior to the enclosure space; positioning the patient within the enclosure space such that the reinforced section is spaced from the patient; inserting an arm of the caregiver through an arm opening in the enclosure portion where the arm opening includes an arm sleeve having a near end, a far end, and a sleeve wall extending therebetween, the near end being joined to the sheet of material about the arm opening, where the sleeve wall extends within the enclosure space; inserting an instrument through a tool opening in the enclosure portion such that an end of the instrument passes from the caregiver-side through the sheet of material to the patient-side and into the enclosure space; and handling the patient or manipulating the instrument through the arm sleeve such that the caregiver can directly visualize the patient through the hygienic barrier.

DESCRIPTION OF THE DRAWINGS

Each of the following figures diagrammatically illustrates aspects of the invention. Variation of the invention from the aspects shown in the figures is contemplated.

DETAILED DESCRIPTION

It is understood that the examples below discuss uses in an endoscopic procedure. However, unless specifically noted, variations of the device and method are not limited to use in endoscopy procedures. Instead, the invention has applicability to any healthcare procedure involving a patient needing to be examined by a medical caregiver. Moreover, the invention can be used in any procedure where the benefits of the method and/or device are desired, but examination of a patient is not occurring.

Figure 2A:
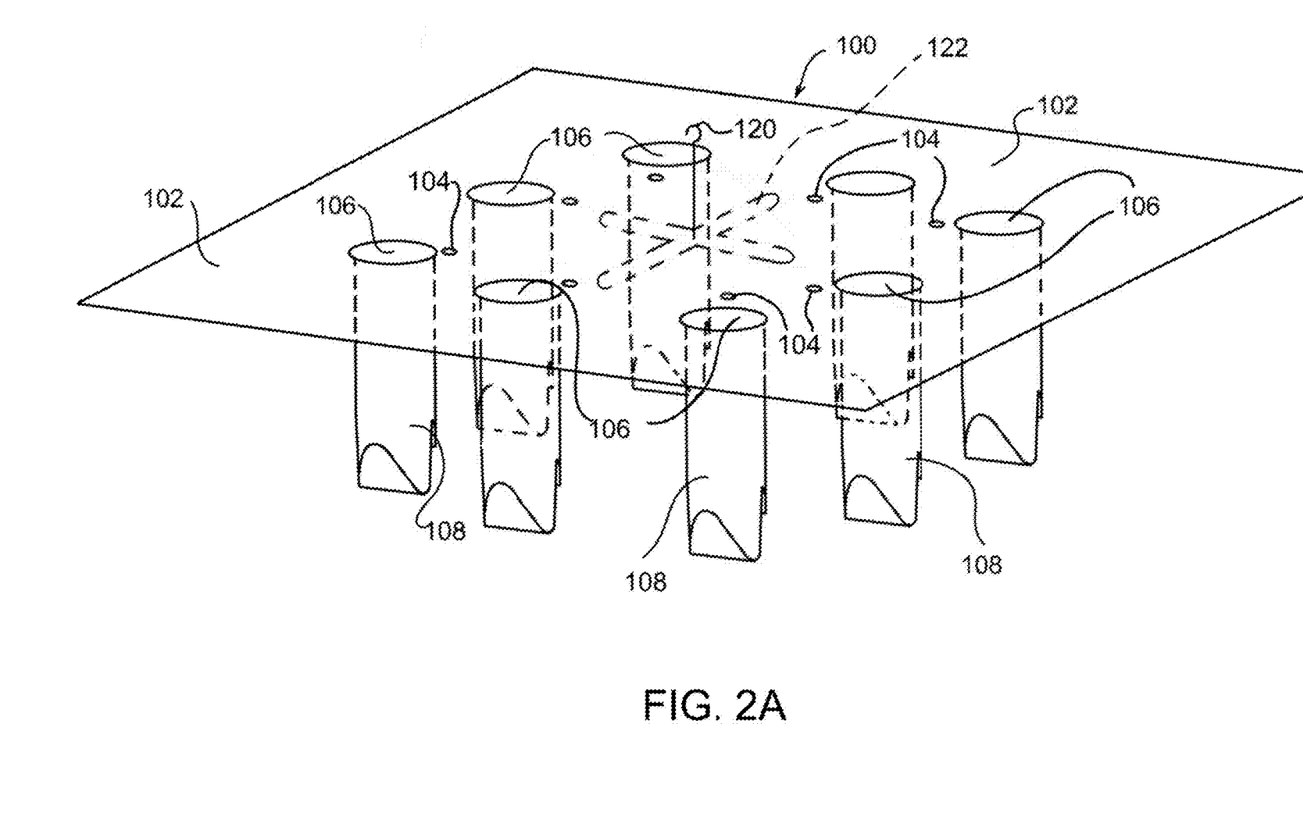
FIG. 2A illustrates a variation of an improved item of personal protective equipment (PPE) comprising a hygienic barrier that blocks transmission of potential pathogens, microorganisms, or other infectious substances residing in a patient.

FIG. 2A illustrates one variation of an improved item of personal protective equipment (PPE) comprising a hygienic barrier 100 that can block transmission of potential pathogens, microorganisms, or other infectious substances residing in a patient. The variation shown in FIG. 2A is illustrated in a flat configuration to better illustrate the components of the hygienic barrier 100. As shown, the hygienic barrier 100 includes a sheet of material 102 that provides a barrier to fluids and other substances as discussed below. The sheet of material 102 can comprise a visually transparent material. Alternate variations can include a semi-transparent or opaque material.

As discussed below, the sheet of material 102 includes a reinforced region and an enclosure portion. In the illustrated variation, the reinforced region is the region supported by a frame 122. The enclosure portion is the region outside of the frame 122 area. In this configuration, when suspended over a patient (e.g., by an attachment feature 120) the enclosure portion drops through the force of gravity about the patient to a deployed configuration. The size of the sheet 102 can be selected to cover the patient (either entirely or partially). Variations include hygienic barriers 100 large enough to hang over a side of an operating table, hospital bed, stretcher, or other structure that supports a patient during examination. The side shown in FIG. 2A can be considered a caregiver side since that is the side that faces the caregiver when the caregiver is attending to a patient within the hygienic barrier 100. In an additional variation, the reinforced region can comprise a heat sealed structure to provide a shape to the sheet 102 as the support. The heat sealed structure can include one or more an integrated loops to provide an attachment structure.

Deployment of the hygienic barrier 100 using a force of gravity provides a number of benefits. For example, the barrier 100 can be spread by a caregiver such that gravity prevents movement of the barrier 100 unless displaced by the caregiver or patient. In addition, deployment of the barrier through the force of gravity allows for quick deployment of the barrier.

The hygienic barrier 100 also includes one or more arm openings 106 located in the enclosure portion of the sheet 102. The arm openings include an arm sleeve 108 that allows the caregiver to insert an arm therethrough and attend to the patient. The arm sleeves include a near end (attached to the sheet 102) and a far end with a sleeve wall extending therebetween. When deployed the enclosure portion forms an enclosure space about the patient and the arm sleeve 108 extends within the enclosure space such that the far end can be moveably positioned in the enclosure space when a caregiver extends a hand/arm into at least one arm opening 108. In such a case, the sleeve 108 and the sheet of material 102 maintain a fluid barrier between the patient and the caregiver. As shown, the distal portion of the arm sleeve 108 can include any number of pockets to accommodate the fingers and thumb of the caregiver. In some variations of the hygienic barrier 100 the arm sleeves 108 are closed at the distal portion. In alternate variations, the arm sleeves 108 can be open. In further variations, a hygienic barrier 100 can include both open end closed arm sleeves.

FIG. 2A also illustrates an optional tool opening 104 adjacent to an arm opening 106. The tool opening 104 allows the caregiver to advance an instrument into the enclosure space at least one tool opening in the enclosure portion that allows an instrument to be passed from the caregiver-side through the sheet of material to the patient-side and into the enclosure space. The tool openings 104 can include a valve or flap. In additional variations, the tool opening 104 can be positioned relative to the arm sleeve 108 such that the arm sleeve itself 108 prevents or blocks fluid from passing through the tool opening.

Figure 2B:
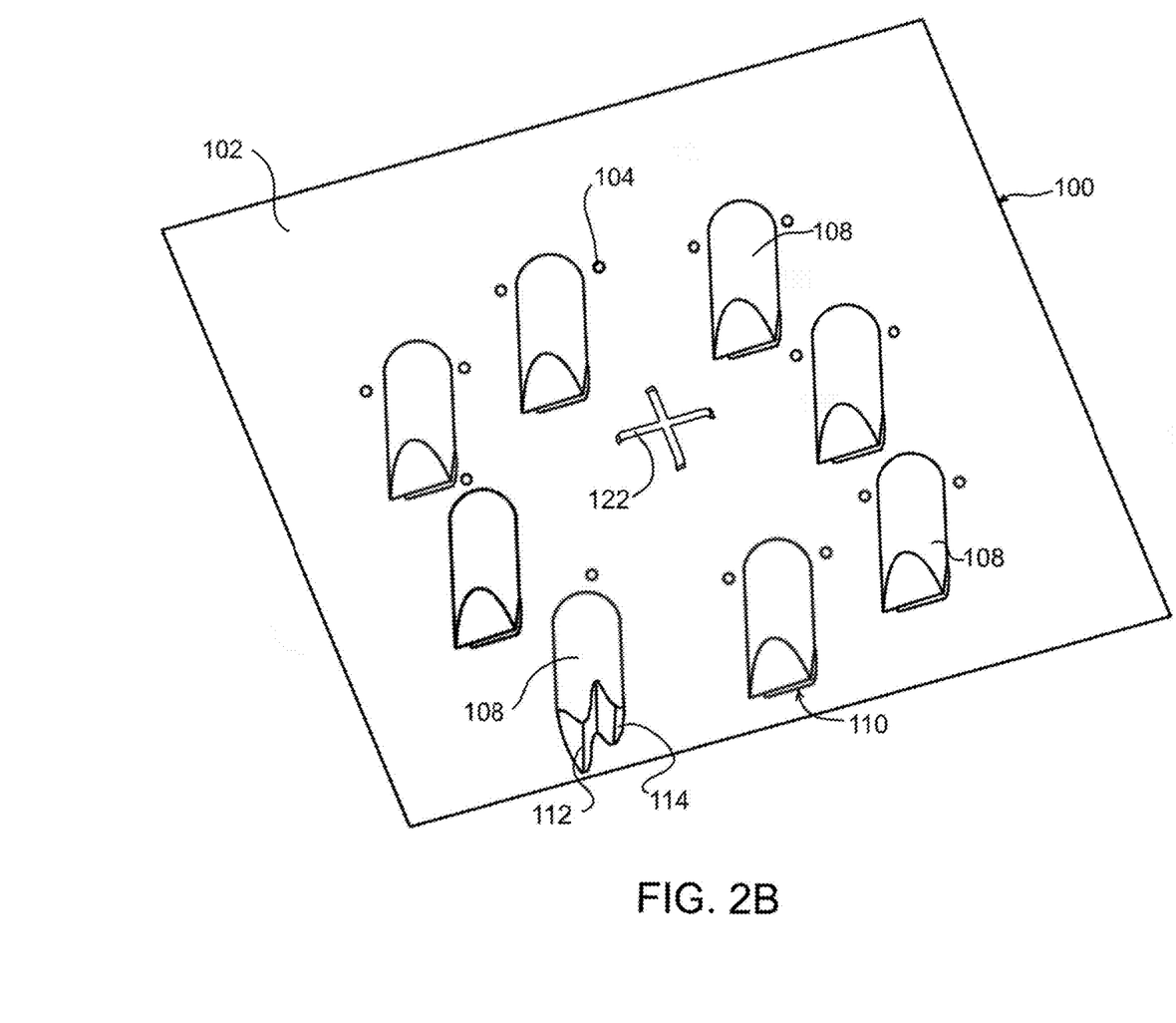
FIG. 2B shows a view of a patient-side of a hygienic barrier similar to that shown in FIG. 2A.

FIG. 2B shows a view of a patient-side of a hygienic barrier 100 similar to that shown in FIG. 2A. As shown, the reinforced portion of the hygienic barrier 100 comprises an area of the sheet 102 having a frame 122 that supports the barrier 100 when suspended. The enclosure portion comprises the area of the barrier 100 that hangs down from the reinforced region and includes one or more arm sleeves 108. This variation of the barrier 100 includes multiple tool openings 104 adjacent to the arm sleeves 108. In addition, the distal portion of the sleeve 108 includes a hand portion 110 comprising a finger pouch/pocket 112 and a thumb pouch/pocket 114 that improve the ability of the caregiver to manipulate instruments or attend to a patient.

Figure 3A:
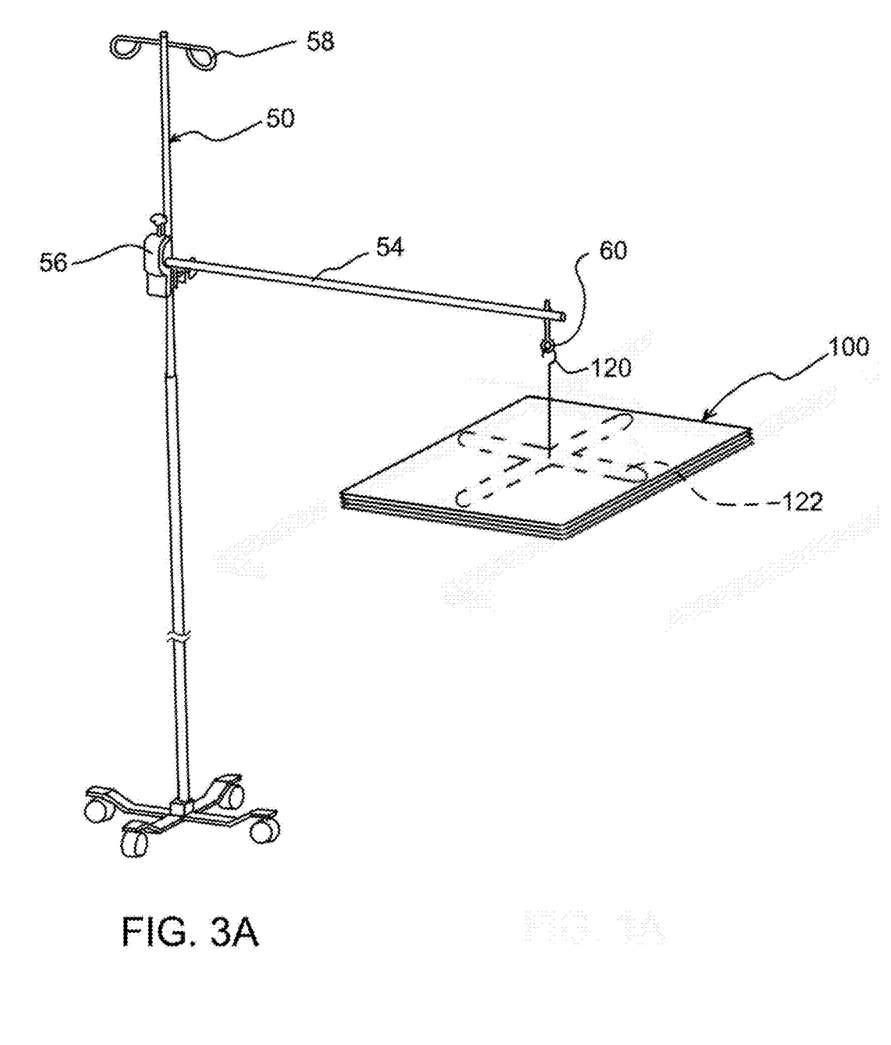
FIG. 3A illustrates an example of a hygienic barrier prior to being deployed.

FIG. 3A illustrates an example of a hygienic barrier 100 prior to being deployed. In this variation, the barrier 100 is shown in a compact folded configuration that is planar. However, other non-planar configurations are within the scope of this disclosure. Typically, the reinforced region (meaning the area of the barrier 100 supported by the frame 122) is coupled to an attachment feature 120 that allows securing of the hygienic barrier 100 to a support structure within the examination area. One example of such a support structure is an IV pole 50. The variation shown in FIG. 3A includes an extension pole 54 that is coupled to the IV pole 50 via a clamp structure 56 and the other end of the extension pole 54 can include one or more eyelets 60 or similar structures for coupling of the attachment feature 120. The optional extension pole 54 allows spacing of the hygienic barrier 100 from the IV pole 50. Alternatively, the hygienic barrier 100 can be directly suspended from one or more hooks 58 of the IV pole 50.

Figure 3B:
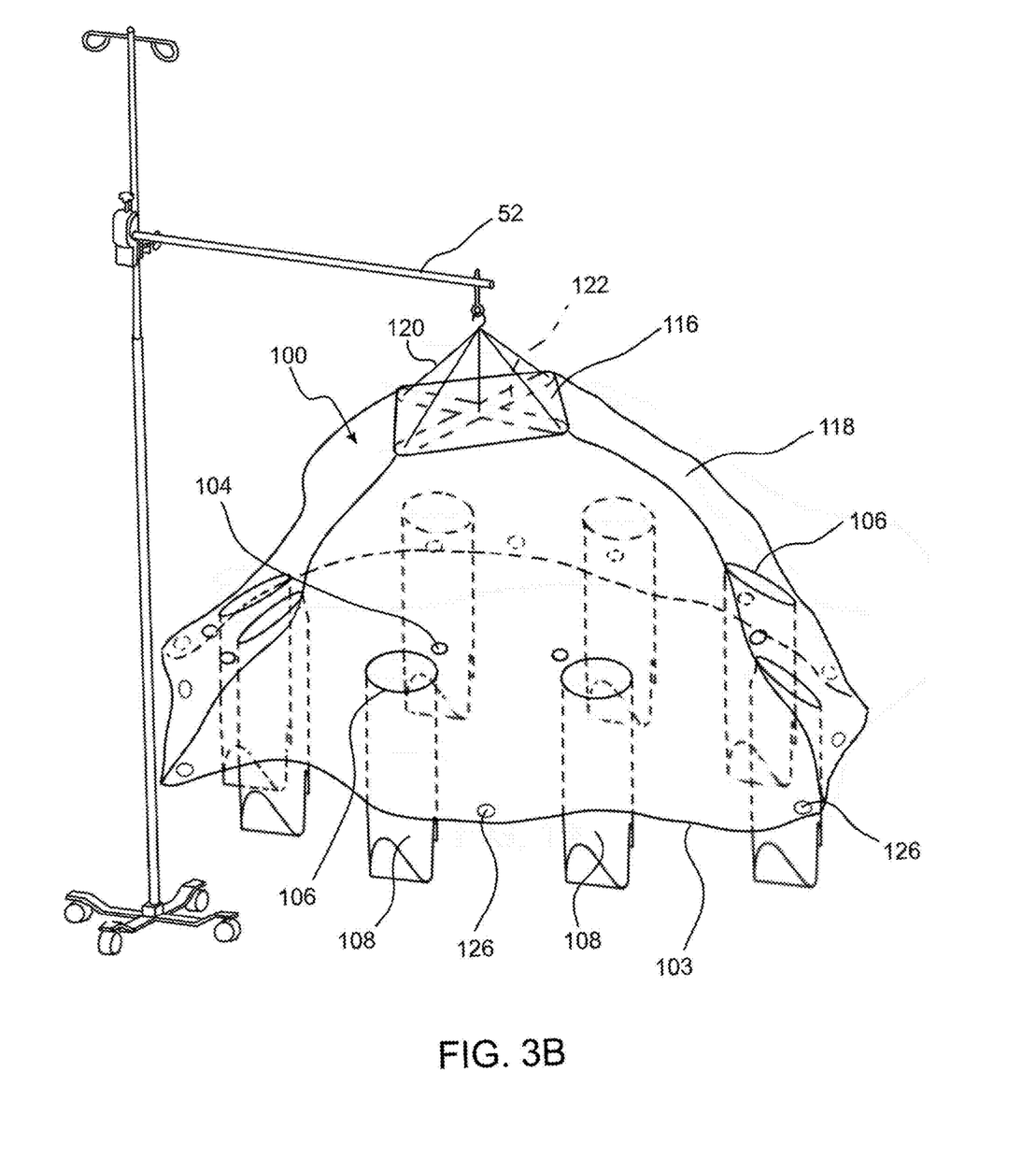
FIG. 3B shows a variation of hygienic barrier in a deployed configuration where a reinforced region of the barrier 100 is suspended from a support to cause an enclosure portion to drop down from the reinforced region through a force of gravity and form an enclosure space.

FIG. 3B shows a variation of hygienic barrier 100 in a deployed configuration. In this variation, after reinforced region 116 of the barrier 100 is suspended from a support (e.g., the extension pole 52) using an attachment feature 120 (such as a hook, wire, string, etc.), the barrier 100 is then released causing the enclosure portion 118 to drop down from the reinforced region 116 through a force of gravity and form an enclosure space. In some variations, the hygienic barrier 100 is pulled towards a deployment configuration. In alternative variations, simply releasing the barrier 100 causes the enclosure portion 118 to drop down. Optionally, the hygienic barrier 100 can include one or more weights or weighted sections 126 to assist with deployment of the barrier 100 as well as to maintain positioning of the end 103 of the barrier 100 during the procedure. Alternatively, or in combination, the sections 126 can comprise temporary fixation structures such as adhesive patches, or hook and loop fasteners.

As noted above, the enclosure portion 118 includes arm openings 106 and arm sleeves 108 as well as instrument openings 104 to allow for a caregiver to attend to a patient positioned within the enclosure space. Variations of the hygienic barrier comprise an enclosure portion that is visually transparent to allows the caregiver to directly visualize the patient through the barrier 100. The reinforced region 116 can be transparent or opaque.

FIG. 3B also illustrates the reinforced region 116 as having a frame 122. In additional variations, the frame 122 can be replaced with a thicker material of sheeting. For example, the reinforced region 116 can comprise a sufficient mil thickness that maintains separation of the enclosure portion 118 directly adjacent to the reinforced region 116. This increases an area of the enclosure space at the top of the hygienic barrier 100 to prevent the barrier from contacting a head of the patient. In additional variations, the reinforced region 116 is not planar but can be concave or have any other shape to increase a spread/area of the enclosure portion 118 and enclosure space at a top of the barrier 100.

Figure 4:
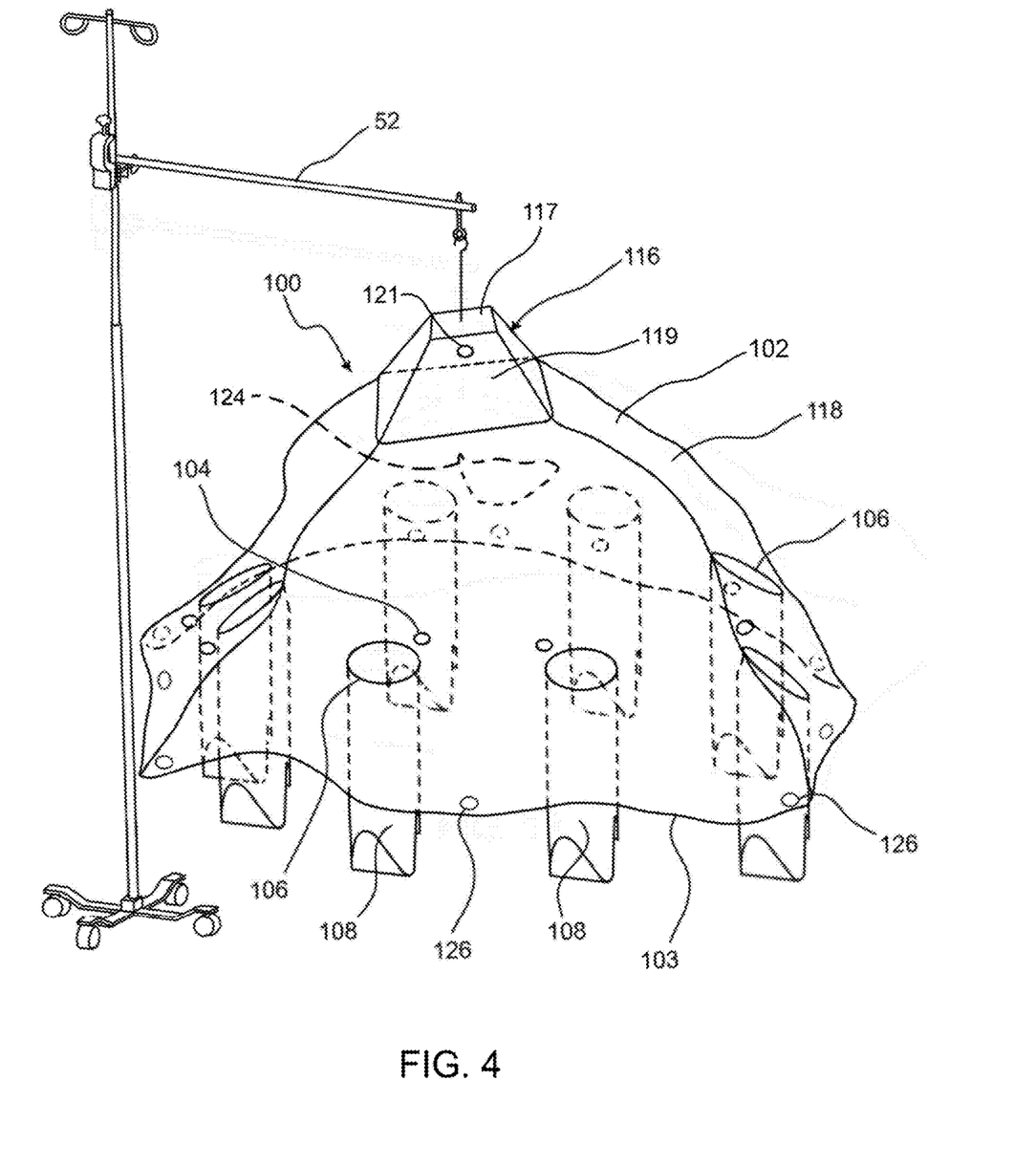
FIG. 4 illustrates another variation of a hygienic barrier with a non-planar reinforced region.

FIG. 4 illustrates another variation of a hygienic barrier with a non-planar reinforced region 116. As shown, this variation of a reinforced region 116 comprises a truncated trapezoidal shape having a top surface 117 and tapered sides 119. The non-planar reinforced region 116 can be formed by shaping the sheet material 102 of the hygienic barrier 100 into a desired shape. Alternatively, the reinforced region 116 can comprise a reinforcement support (as discussed below). In additional variations, the non-planar reinforced region 116 can comprise a separate shaped material having the desired shape where the sheet material 102 is sealed to the shaped material. FIG. 4 also shows the reinforced region 116 including one or more tool/instrument openings 121, which can be used to position a source of illumination, positive pressure (to assist in spreading the enclosure portion 118), ventilation, suction, UVC illumination source (for additional antimicrobial and antiviral properties).

FIG. 4 also illustrates a hygienic barrier including one or more pockets 124 on a patient side to allow a caregiver to store products and items needed during the procedure or used during the procedure. Such pockets 124 can be positioned on the caregiver-side as well. Alternatively, the caregiver can use one or more arm sleeves 108 as pockets.

Figure 5:
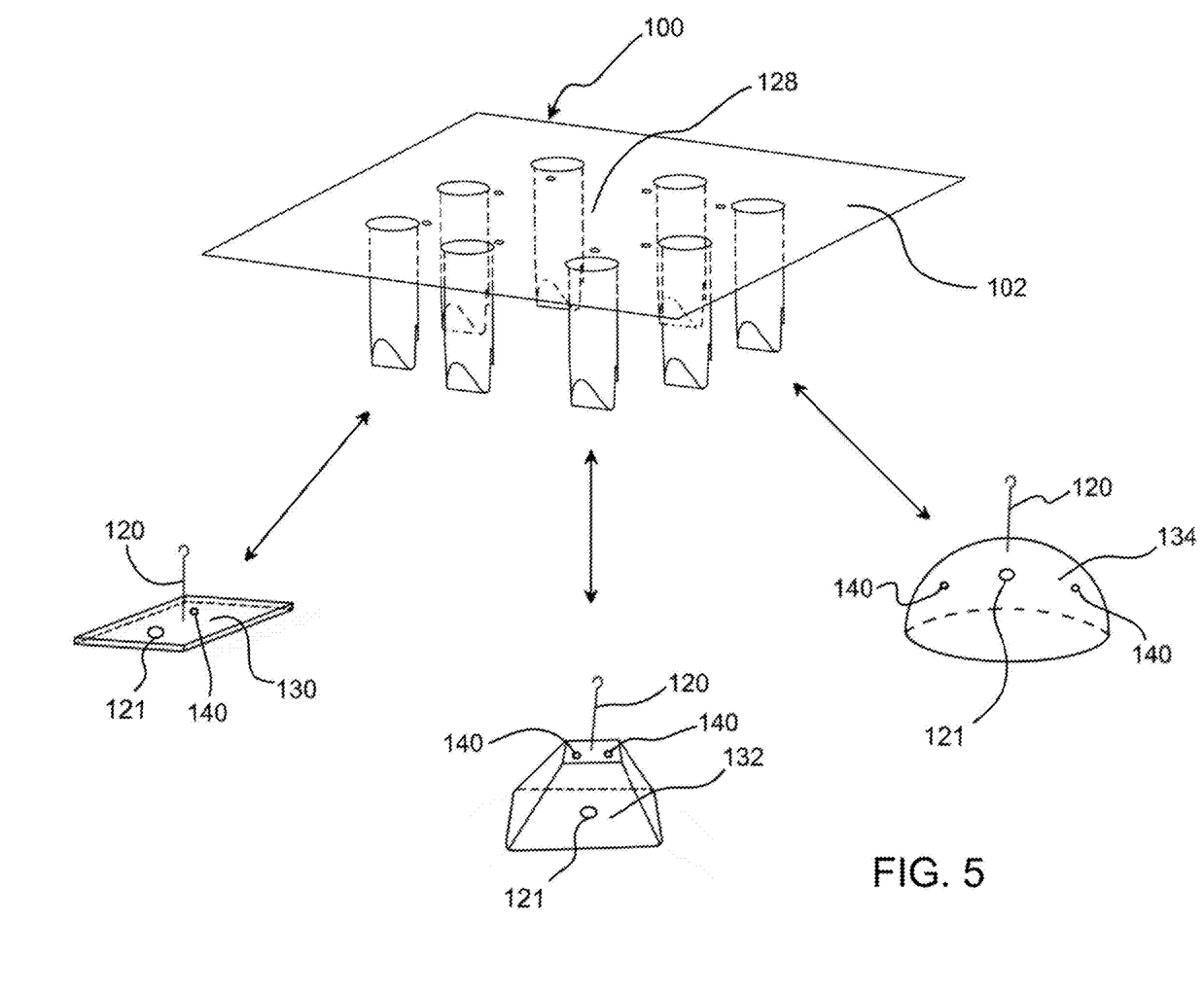
FIG. 5 shows an additional variation of a hygienic barrier where the barrier comprises a sheet of material positioned on one or more reinforcement supports/frames.

FIG. 5 shows an additional variation of a hygienic barrier 100 where the barrier comprises a sheet of material 102 that is positioned on one or more reinforcement supports/frames 130, 132, 134. In such a variation, an attachment feature 120 can be inserted through a center region 128 of the hygienic barrier 100. The reinforcement supports/frames 130, 132, 134 can comprise any material that provides the desired shape. In addition, though not shown in FIG. 5, the reinforcement supports 130, 132, 134 can include one or more openings 121 for insertion of tools therethrough. In use the sheet 102 is draped over the 130, 132, 134, such that the portion of the sheet 102 contacting the support 130, 132, 134 becomes the reinforced region of the barrier 100 with the remaining surface of the sheet 102 forming the enclosure portion. The support structures 130, 132, 134 can be fabricated from polymers or metal alloys to provide a reusable barrier component. In additional variations, the support structures 130, 132, 134 can be fitted with illumination sources such as LEDs 140 on an interior surface or exterior surface to provide illumination, sterilization, etc. As shown, the support frame 130 can be planar or can be configured as non-planar 132, 134 with an internal volume. However, any number of shapes are within the scope of this disclosure.

Figure 6:
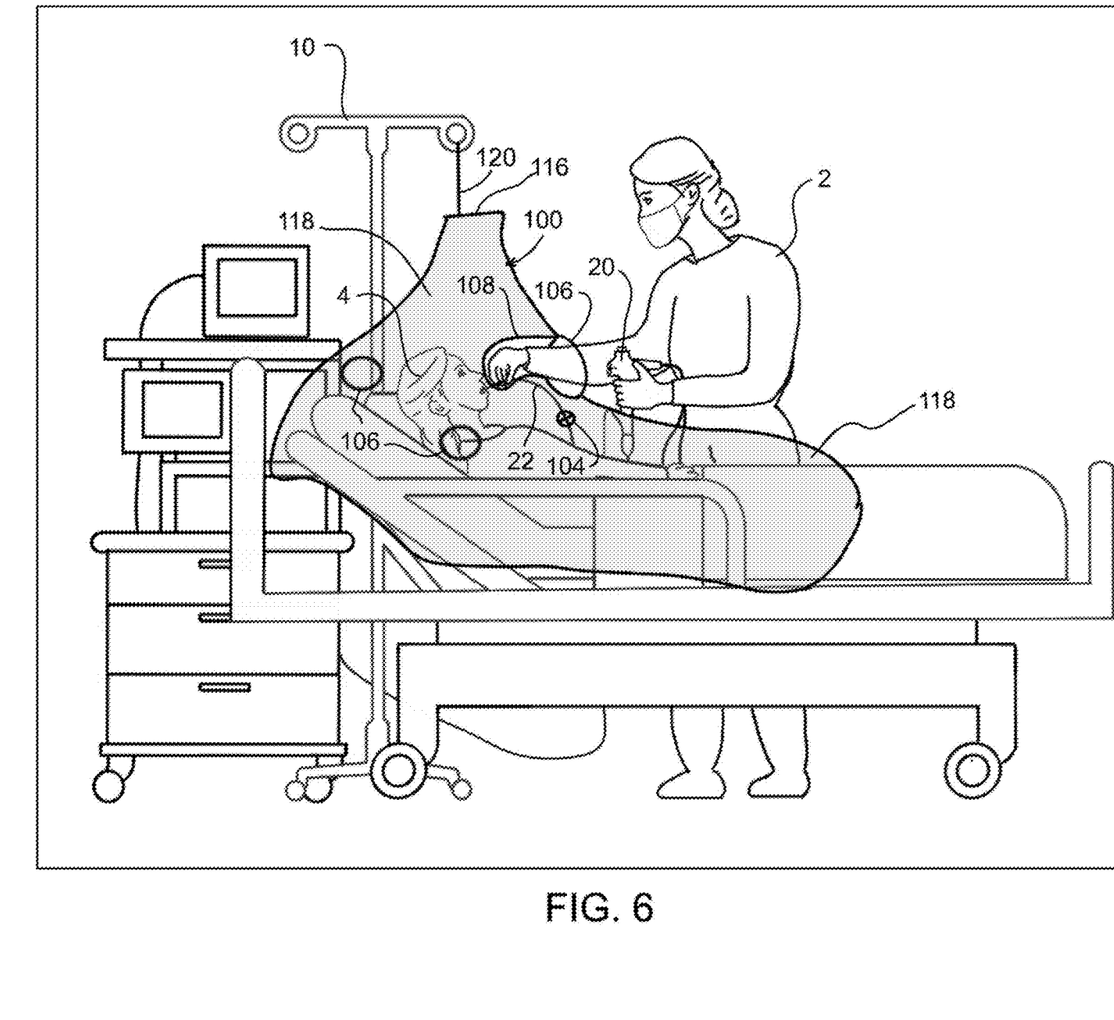
FIG. 6 illustrates one example of the use of a hygienic barrier that provides a protective fluid barrier between a caregiver and a patient.

FIG. 6 illustrates one example of the use of a hygienic barrier 100 that provides a protective fluid barrier between a caregiver 2 and a patient 4. The barrier 100 can be used in sterile environments as well as convention non-sterile examination settings. As shown, the barrier 100 is suspended from a structure (e.g., an IV pole 10) using any number of attachment features 120. In the illustrated variation, the reinforced region 116 is suspended at a distance away from the patient 4. This allows the enclosure portion 118 to taper or spread away from the reinforced region 116 resulting in the enclosure space (i.e., the space bounded by the interior of the enclosure portion 118) having an increased area to accommodate the patient 4. As shown, the caregiver 2 can insert an arm through an arm opening 106 and arm sleeve 108 to manipulate an instrument 22 that is advanced through an instrument opening. 104. The shape and structure of the arm sleeves 108 (as discussed herein) allow for the caregiver 2 to attend to the patient as well as administer tools/instruments relative to the patient. The arm openings 106, sleeves 108, and tool/instrument openings 104 can be positioned about the enclosure portion 108. In one example, it was found that a hygienic barrier having an 8 to 10 foot diameter was sufficient to cover a patient in a hospital environment. However, any size range is within the scope of this disclosure.

Figure 7A:
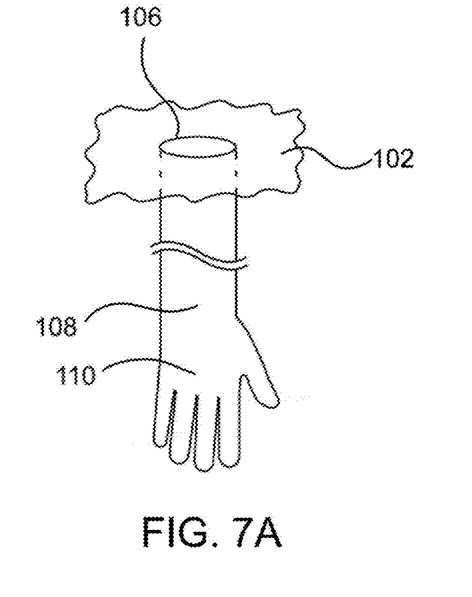
FIGS. 7A to 7D illustrate some examples of variations of arm sleeves for use with the hygienic barriers described herein.
Figure 7B:
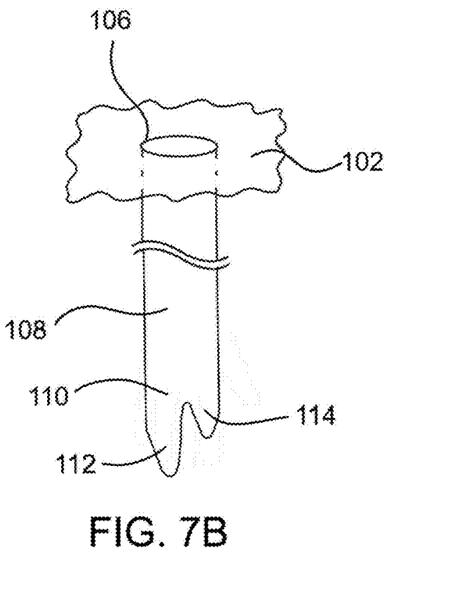
Figure 7C:
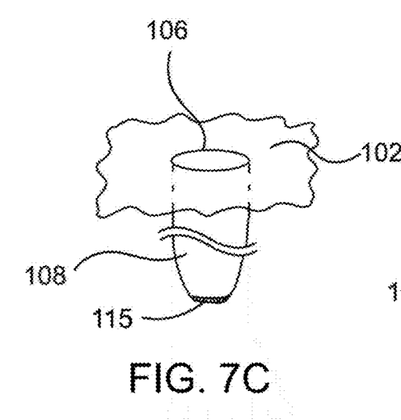
Figure 7D:
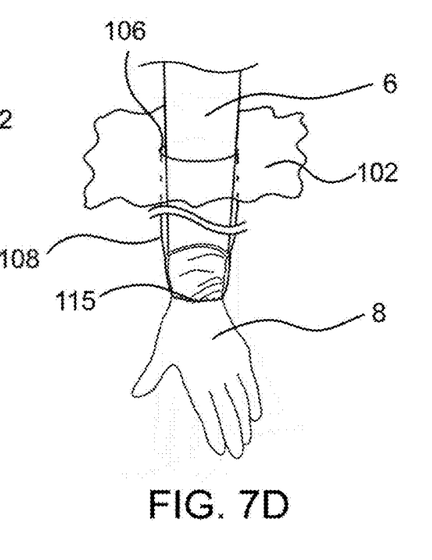

FIGS. 7A to 7D illustrate some examples of variations of arm sleeves 108 for use with the hygienic barriers described herein. FIG. 7A illustrate an arm sleeve 106 extending from an opening 106 in a sheet of material 102, where the arm sleeve 108 includes a hand portion 110 shaped in a glove. FIG. 7B illustrates an arm sleeve 108 having a hand portion 110 having a finger pouch/pocket 112 with an opposable thumb pouch/pocket 114. In these variations, the arm sleeve 108 is sealed at the hand portion 110 to prevent contamination from passing through the barrier. FIG. 7C illustrates another variation of an arm sleeve 108 where a hand portion is replaced with a closure section 115. In this example, the arm sleeve 108 is open at a far end but, as shown in FIG. 7D, this variation allows for a caregiver to advance an arm 6 through the opening 106 and arm sleeve 108 such that the closure portion 115 closes about a hand/glove 8 of the caregiver. The closure section 115 can comprise an elastic band that allows for advancement of a hand 8 therethrough. Alternatively, the closure section 115 can comprise a plastically deformable opening. It is noted that the arm sleeves can also function as pockets to allow a caregiver to store any materials for use in or from the procedure.

Figure 8A:
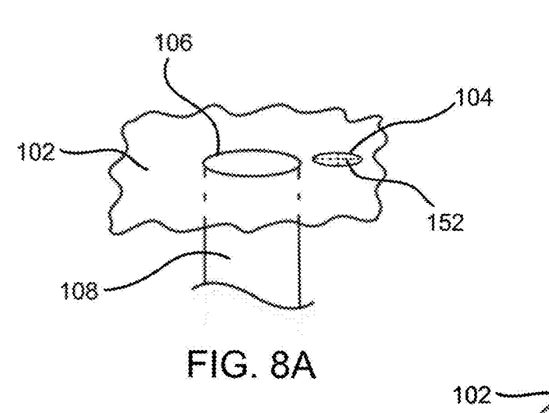
FIGS. 8A to 8D illustrate additional variations of instrument openings for use with variations of hygienic barriers as discussed herein.

FIGS. 8A to 8D illustrate additional variations of instrument openings 104 for use with variations of hygienic barriers as discussed herein. The figures show instrument openings 104 adjacent to arm openings 106 on a caregiver-side of the barrier. However, the same configurations can be placed on the patient-side of the barrier as well. FIG. 8A illustrates an instrument opening 104 that can comprise an opening in a layer 102. As noted above, the opening can comprise a slit 152 or perforations. Alternatively, the opening 104 can simply be a removed section of the sheet 102. Alternatively, the opening 104 can comprise one or more flaps that meet along edge 152.

Figure 8B:
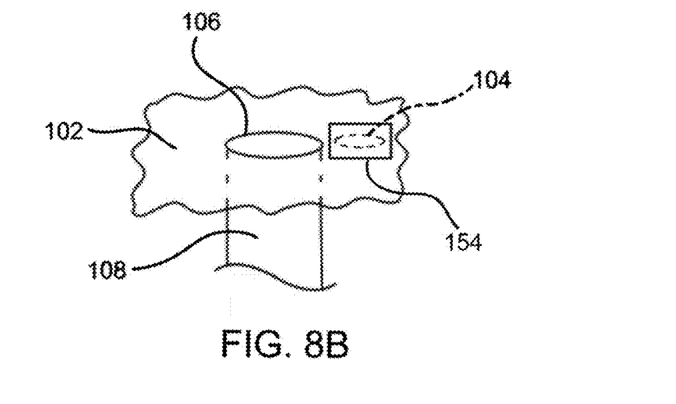

FIG. 8B illustrates an instrument opening 104 that is covered by one or more flaps 154 of material. The flaps 154 can be placed on the patient-side, caregiver-side, or both sides of the barrier. In one variation, a single edge of the flap 154 is affixed to the sheet 102 so that the flap can be pulled back (or pushed in) to allow passage of an instrument.

Figure 8C:
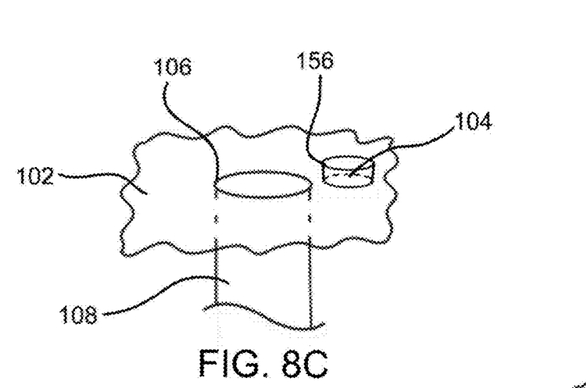

FIG. 8C illustrates an opening 104 as having a sleeve 156. The length of sleeve 156 is shown for illustration only. Variations of the instrument sleeve 156 can extend on either side of the barrier. Moreover, the instrument sleeve 156 can extend with the arm sleeve 108.

Figure 8D:
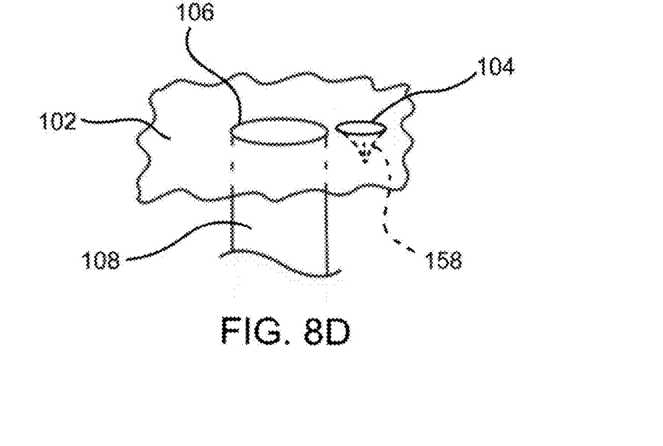

FIG. 8D shows an instrument opening 104 including a valve 158. For example, the valve 158 can comprise a duckbill valve or any membrane valve that allows passage of an instrument therethrough.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described. For example, the invention includes combinations of aspects of the variations of the devices described herein as well as the combination of the variations themselves. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

I claim:

1. A hygienic barrier for suspending over a patient to limit a spread of fluids, the hygienic barrier comprising:
   a reinforced region that maintains a predetermined shape prior to deployment and after suspending over the patient;
   an enclosure portion that encircles the reinforced region, where the reinforced region comprises a planar shape and remains transverse to the patient, such that when in a deployed configuration, the reinforced region maintains the predetermined shape allowing the enclosure portion to hang down and spread outward from the reinforced region through a force of gravity to form an enclosure space having a greater perimeter than the reinforced region, where at least the enclosure portion allows for direct visualization of the patient therethrough, and wherein the reinforced region and the enclosure portion comprise a continuous sheet of material;
   the enclosure portion having a patient-side on an interior of the enclosure space and a caregiver-side exterior to the enclosure space;
   at least one arm opening located in the enclosure portion, the at least one arm opening includes an arm sleeve, the arm sleeve having a near end, a far end, and a sleeve wall extending therebetween, the near end being joined to the enclosure portion about a respective arm opening, where the sleeve wall extends within the enclosure space such that the far end can be moveably positioned in the enclosure space when a caregiver extends a hand into at least one arm opening from the caregiver-side, where the arm sleeve and the enclosure portion maintain a fluid barrier between the patient and the caregiver; and
   at least one tool opening in the enclosure portion that allows an instrument to be passed from the caregiver-side through the enclosure portion to the patient-side and into the enclosure space.

2. The hygienic barrier of claim 1, wherein the reinforced region includes a reinforcement support structure.

3. The hygienic barrier of claim 1, wherein the at least one tool opening is located adjacent to the at least one arm opening.

4. The hygienic barrier of claim 1, wherein the reinforced region comprises a frame structure adjacent to the reinforced region.

5. The hygienic barrier of claim 1, wherein the reinforced region bends to a lesser degree than the enclosure portion to create an increased area of the enclosure space adjacent to the reinforced region.

6. The hygienic barrier of claim 1, wherein the far end of the arm sleeve comprises a glove shape with at least two opposable portions.

7. The hygienic barrier of claim 6, wherein the glove shape comprises four finger portions and a thumb portion.

8. The hygienic barrier of claim 1, further comprising a valve structure located in the at least one tool opening.

9. The hygienic barrier of claim 1, further comprising a temporary barrier in the at least one tool opening.

10. The hygienic barrier of claim 1, further comprising at least two overlapping flaps in the at least one tool opening.

11. The hygienic barrier of claim 1, wherein a far end of the arm sleeve comprises a hand opening surrounded by an elastic portion, such that when the caregiver extends the hand into the hand opening and through the hand opening, the elastic portion causes the sleeve wall to close about the hand or an arm of the caregiver.

12. The hygienic barrier of claim 1, wherein an outer perimeter of the enclosure portion is weighted relative to an inner perimeter of the enclosure portion.

13. The hygienic barrier of claim 1, further comprising at least one or more pockets on the caregiver-side of the enclosure portion.

14. The hygienic barrier of claim 1, further comprising at least one or more pockets on the patient-side of the enclosure portion.

15. The hygienic barrier of claim 1, wherein the enclosure portion is frameless.

16. The hygienic barrier of claim 1, further comprising an attachment arm coupled to the reinforced region, where the attachment arm can be detachably coupled to an external structure to suspend the hygienic barrier.

17. The hygienic barrier of claim 1, further comprising a pre-deployment configuration wherein the enclosure portion is folded in a flat shape.

18. The hygienic barrier of claim 1, wherein an entirety of the enclosure portion allows for direct visualization of the patient therethrough.

19. A method for establishing a hygienic barrier between a caregiver and a patient, the method comprising:
   suspending a reinforced section of a sheet of material above the patient, where the reinforced section maintains a planar shape prior to deployment and after suspending over the patient, where the planar shape is transverse to the patient such that gravity causes an enclosure portion of the sheet of material to hang down and spread outward from the reinforced section, without changing the planar shape to form an enclosure space about the patient having a greater perimeter than the reinforced section, where a patient-side of the sheet of material is located on an interior of the enclosure space and a caregiver-side of the sheet of material is exterior to the enclosure space;

wherein the enclosure portion includes one or more arm openings, and at least one of the one or more arm openings includes an arm sleeve having a near end, a far end, and a sleeve wall extending therebetween, the near end being joined to the sheet of material about a respective arm opening, where the sleeve wall extends within the enclosure space;

wherein the enclosure portion includes at least one tool opening that allows an instrument to be passed from the caregiver-side through the sheet of material to the patient-side and into the enclosure space; and wherein the caregiver inserts a hand into the sleeve wall through the one or more arm openings and to the far end allowing for the caregiver to manipulate the instrument while the sleeve wall and the sheet of material maintains the hygienic barrier between the caregiver and the patient allowing the caregiver to attend to and directly visualize the patient through the hygienic barrier.

20. A method for a caregiver to interact with a patient through a hygienic barrier using an support structure within an examination area, the method comprising:

suspending an attachment feature from the support structure and over the patient, where the attachment feature is coupled to a reinforced section of a sheet of material that maintains a predetermined shape prior to deployment and after suspending over the patient, where the predetermined shape is transverse to the patient such that gravity causes an enclosure portion of the sheet of material to hang down and spread outward from the reinforced section without changing the predetermined shape to form an enclosure space having a greater perimeter than the reinforced section, such that a patient-side of the sheet of material is located on an interior of the enclosure space and a caregiver side of the sheet of material is exterior to the enclosure space;

positioning the patient within the enclosure space such that the reinforced section is spaced from the patient;

inserting an arm of the caregiver through an arm opening in the enclosure portion where the arm opening includes an arm sleeve having a near end, a far end, and a sleeve wall extending therebetween, the near end being joined to the sheet of material about the arm opening, where the sleeve wall extends within the enclosure space;

inserting an instrument through a tool opening in the enclosure portion such that an end of the instrument passes from the caregiver-side through the sheet of material to the patient-side and into the enclosure space; and handling the patient or manipulating the instrument through the arm sleeve such that the caregiver can directly visualize the patient through the hygienic barrier.

21. The method of claim 20, wherein the instrument comprises a device selected from the group consisting of an illumination device, a positive pressure device, a ventilation device, a suction device, a UVC illumination device.

\* \* \* \* \*